US012635922B2

(12) United States Patent
Samproni

(10) Patent No.: US 12,635,922 B2
(45) Date of Patent: May 26, 2026

(54) SENSOR ARRAY

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 534 days.

(21) Appl. No.: 18/044,128

(22) PCT Filed: Aug. 30, 2021

(86) PCT No.: PCT/US2021/048179
§ 371 (c)(1),
(2) Date: Mar. 6, 2023

(87) PCT Pub. No.: WO2022/055737
PCT Pub. Date: Mar. 17, 2022

(65) Prior Publication Data
US 2023/0329606 A1     Oct. 19, 2023

Related U.S. Application Data

(60) Provisional application No. 63/076,171, filed on Sep. 9, 2020.

(51) Int. Cl.
*A61B 5/15*          (2006.01)
*A61B 5/00*          (2006.01)

(52) U.S. Cl.
CPC .... *A61B 5/150961* (2013.01); *A61B 5/15087* (2013.01); *A61B 5/6829* (2013.01); *A61B 2503/045* (2013.01); *A61B 2560/0242* (2013.01)

(58) Field of Classification Search
USPC ...................................................... 73/40.5 R
See application file for complete search history.

(56) References Cited

U.S. PATENT DOCUMENTS

| | | | |
|---|---|---|---|
| 5,046,496 A | 9/1991 | Betts et al. | |
| 6,123,820 A | 9/2000 | Bergkuist et al. | |
| 6,193,864 B1 | 2/2001 | Leader et al. | |
| 6,326,612 B1 | 12/2001 | Elkind et al. | |
| 7,122,152 B2 * | 10/2006 | Lewis ................ | G01N 33/0031 422/50 |
| 7,595,023 B2 * | 9/2009 | Lewis ................ | G01N 33/0031 422/62 |
| 11,154,859 B2 * | 10/2021 | Pudduck ........... | B01L 3/502715 |
| 12,188,922 B2 * | 1/2025 | Pudduck ............... | G01N 33/49 |
| 2005/0171449 A1 * | 8/2005 | Suslick ................ | G01N 21/272 436/164 |

(Continued)

OTHER PUBLICATIONS

International Search Report and Written Opinion of International Application No. PCT/US2021/048179 dated Nov. 30, 2021.

*Primary Examiner* — Walter L Lindsay, Jr.
*Assistant Examiner* — Warren K Fenwick

(57) ABSTRACT

A sensor array is disclosed. The sensor array includes a fluid inlet, a fluid outlet, a flow path extending between the fluid inlet and the fluid outlet; and at least one optimization sensor positioned outside of the flow path of the sensor array and configured to provide at least one performance parameter of the sensor array. The at least one performance parameter having performance data of the sensor array.

17 Claims, 9 Drawing Sheets

(56)  References Cited

U.S. PATENT DOCUMENTS

| | | | |
|---|---|---|---|
| 2007/0132043 A1* | 6/2007 | Bradley | B82Y 10/00 |
| | | | 257/414 |
| 2009/0060789 A1 | 3/2009 | Aas et al. | |
| 2013/0077097 A1 | 3/2013 | Engstrand | |
| 2014/0039351 A1* | 2/2014 | Mix | G16H 40/20 |
| | | | 600/587 |
| 2014/0366612 A1 | 12/2014 | Horne et al. | |
| 2015/0037170 A1 | 2/2015 | Burdi et al. | |
| 2017/0143886 A1 | 5/2017 | Wilt et al. | |
| 2017/0197212 A1* | 7/2017 | Deshpande | B01L 3/502715 |
| 2018/0182228 A1 | 6/2018 | Alcorn et al. | |
| 2018/0266972 A1* | 9/2018 | Samproni | H05K 1/189 |
| 2018/0283818 A1 | 10/2018 | Victor et al. | |
| 2021/0015377 A1* | 1/2021 | Wei | A61B 5/0245 |

* cited by examiner

300

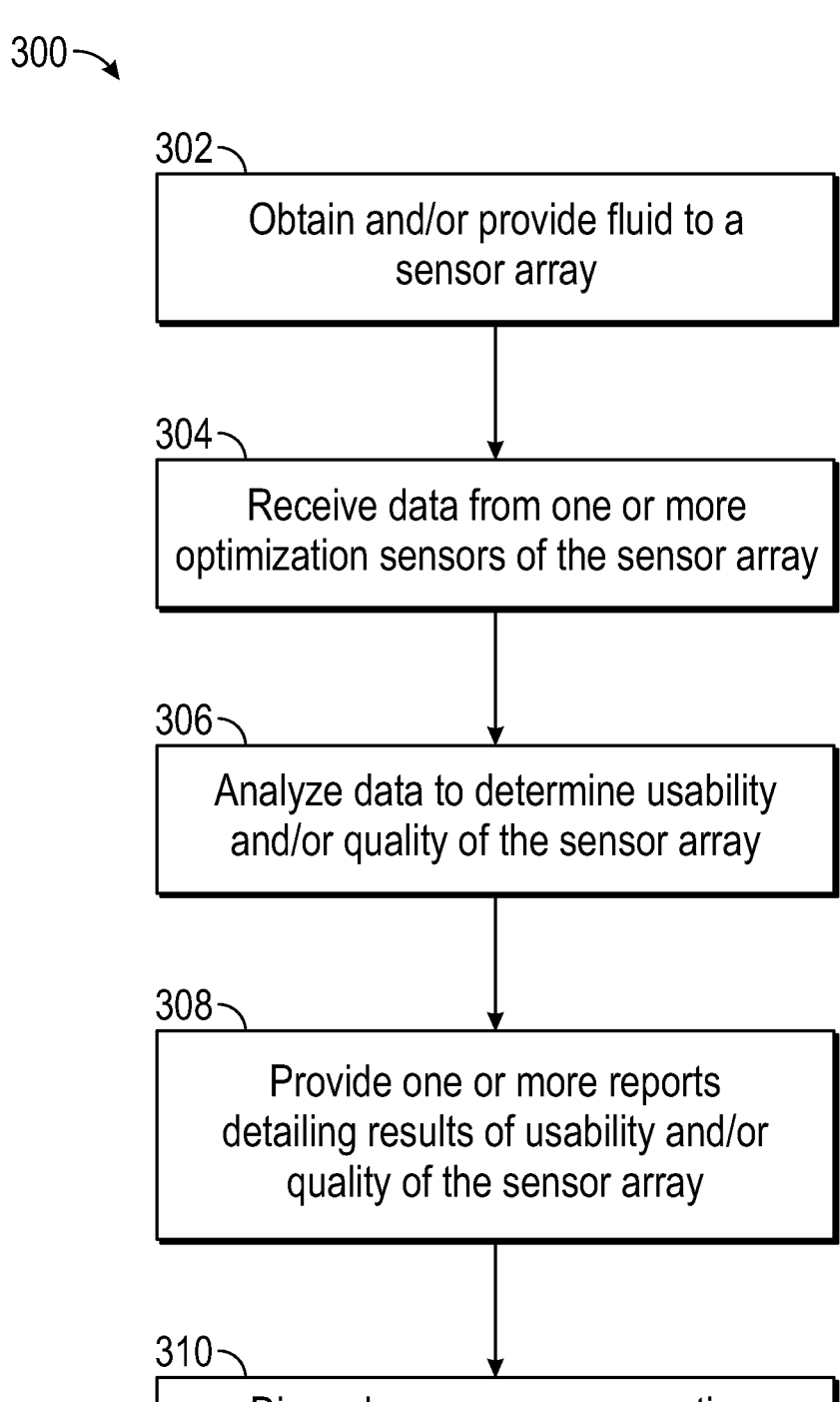

302
Obtain and/or provide fluid to a
sensor array

304
Receive data from one or more
optimization sensors of the sensor array

306
Analyze data to determine usability
and/or quality of the sensor array

308
Provide one or more reports
detailing results of usability and/or
quality of the sensor array 310
Discard sensor array or continue
analysis of fluid based on results of
usability and/or quality of the
sensor array

FIG. 12

SENSOR ARRAY

This application claims benefit under 35 USC § 119(e) of U.S. Provisional Application No. 63/076,171, filed Sep. 9, 2020. The entire contents of the above-referenced patent application(s) are hereby expressly incorporated herein by reference.

FIELD OF THE DISCLOSURE

The disclosure herein generally relates to the field of sensors. Such sensors may be used in the analysis of fluid properties, including gas and liquid.

BACKGROUND

Recent evolution within the industry looks to provide blood analysis using smaller sample sizes while retaining the multitude of data needed to make accurate diagnosis. Heel sticks and draws from arterial lines are the most commonly used sites for blood draws of infants. Heel sticks require a high degree of technical expertise to be done properly and without inflicting unnecessary pain or harm to the patient. Frequent blood draws for laboratory testing create the risk of iatrogenic anemia. It has been estimated that 64% of infants <1500 g receive transfusions for anemia due in part to frequent or excessive blood draws. With a plasma volume of 4-5% of body weight, a 1,500 g infant has a total of 70 mL of plasma. Blood transfusion may be required when 10% or more of a neonate's blood volume is withdrawn in 2-3 days. This amount represents about 80 mL/kg of body weight for a full-term infant, and about 100 mL/kg for a preterm infant.

The volume and number of blood draws have been reduced in recent years due to transcutaneous monitoring and newer equipment. Minimizing the volume of blood needed for each blood draw may reduce the subsequent need for transfusion as well as the risk associated with transfusion. Many of the current clinical chemistry analyzers are moving towards small blood sample volumes for testing, with many sensor arrays requiring between 45 μL to 400 μL, depending on the number of analytes being measured (e.g., blood gases, electrolytes, etc.).

Performing blood analysis using a small blood sample provides a relatively large number of samples to be used in a relatively short amount of time and/or smaller volumes of blood. Infants are not the only patients suffering during blood draws. Patients in intensive care may require a sampling frequency of 15-20 per day for blood gas and clinical chemistry measurements, leading to a potentially large loss of blood during patient assessment. As such, the prospect of utilizing small volumes of blood, while still providing accurate analytics is worthwhile.

In addition, by reducing the size of the analyzer sufficiently to make the unit portable, analysis may be performed at the point of care. Point of care allows the diagnosis to be provided external to the laboratory giving a clinician the gift of time when an accurate and quick diagnosis may be needed. Point of care sensor arrays may permit in vitro analysis at the patient's bedside, in the emergency room, or in the intensive care unit.

Generally, a sensor analytic system requiring small volumes of blood may include a multitude of sensors within a flow path. The sensors may be capable of analyzing the fluid for one or more analytes within the same sensor array. Such sensor arrays, however, may contain bonding points having the potential to leak as fluid flows through the flow path of the sensor array. Additionally, pressure may continuously build within the flow path (e.g., blood clot) adding force pushing fluid through the flow path at an undesired pace. Further, as the industry moves towards point of care systems, environmental considerations, including handling during shipping and storage, may influence the accuracy of the systems. As such, there exists a need within the art to monitor potential sensor array failure due to bonding, pressure and environment concerns including humidity, light, corrosion, and temperature.

BRIEF DESCRIPTION OF THE DRAWINGS

Like reference numerals in the figures represent and refer to the same or similar element or function. Embodiments of the present disclosure may be better understood when consideration is given to the following detailed description thereof. Such description makes reference to the annexed pictorial illustrations, schematics, graphs, drawings, and appendices. In the drawings:

FIG. 12 is an exemplary method for determining usability and/or quality of a sensor array in accordance with the present disclosure.

DETAILED DESCRIPTION OF EXEMPLARY EMBODIMENTS

Figure 1:
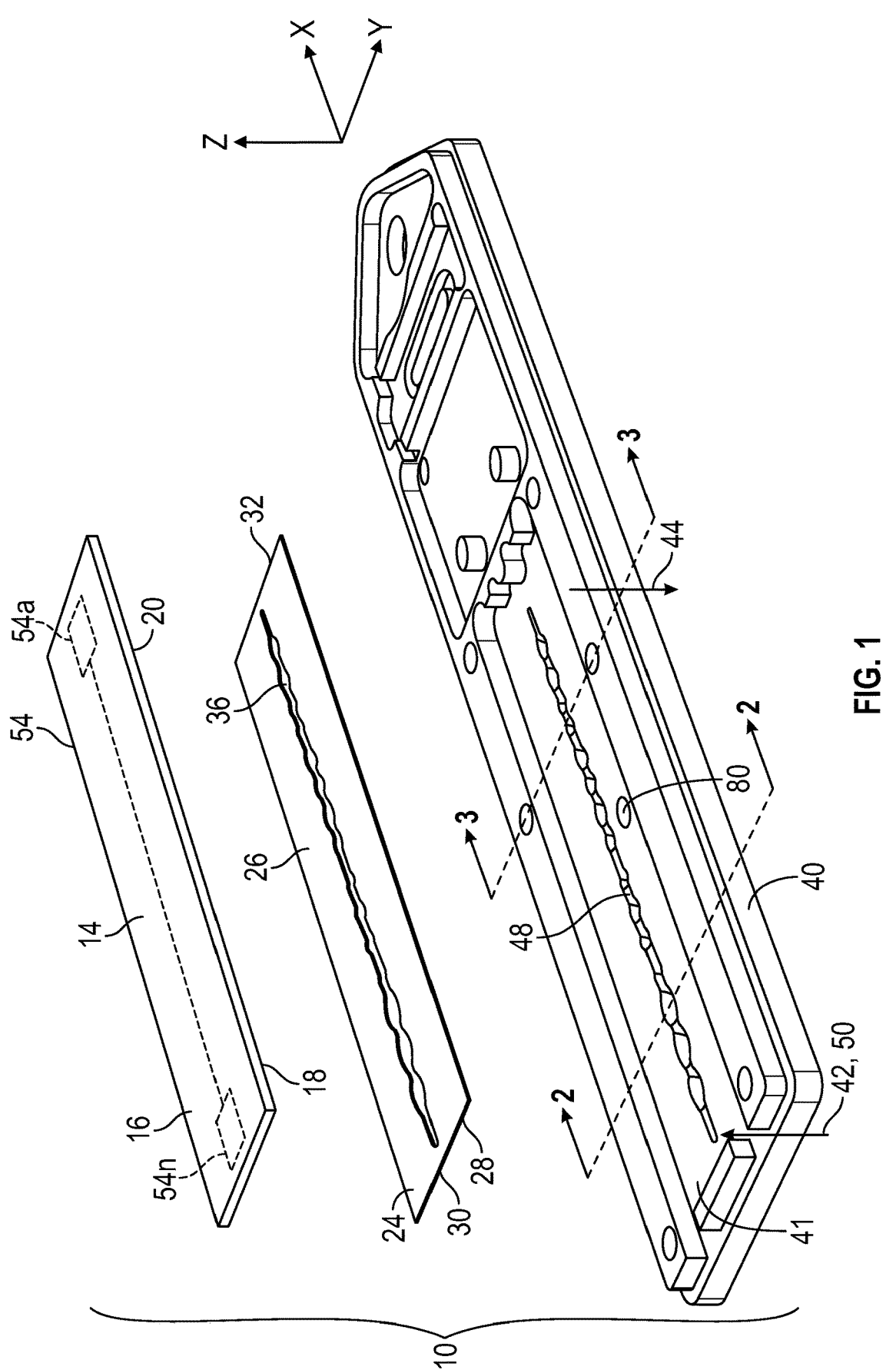
FIGS. 1-4, 5A, and 5B illustrate an exemplary embodiment of a sensor array having one or more optimization sensors in accordance with the present disclosure.

Before explaining at least one embodiment of the present disclosure in detail, it is to be understood that embodiments of the present disclosure are not limited in their application to the details of construction and the arrangement of the components or steps or methodologies set forth in the following description or illustrated in the drawings. The inventive concepts in the present disclosure are capable of other embodiments or of being practiced or carried out in various ways. Also, it is to be understood that the phraseology and terminology employed herein is for the purpose of description and should not be regarded as limiting.

In this detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, language such as "including," "comprising," "having," "containing," or "involving," and variations thereof, is intended to be broad and encompass the subject matter listed thereafter, equivalents, and additional subject matter not recited or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes slight variations or deviations therefrom, caused by measuring error, manufacturing tolerances, stress exerted on various parts, wear and tear, or combinations thereof, for example.

The use of the term "at least one" will be understood to include one and any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Circuitry, as used herein, could be analog and/or digital components, or one or more suitably programmed microprocessors and associated hardware and software, or hardwired logic. Also, certain portions of the implementations may be described as "components" that perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transitory memory. Exemplary non-transitory memory includes random access memory, read only memory, flash memory or the like. Such non-transitory memory can be electrically based or optically based.

As used herein any reference to "one embodiment" or "an embodiment" means that a particular element, feature, structure, or characteristic described in the embodiment is included in at least one embodiment. The appearances of the phrase "in one embodiment" in various places in the specification are not necessarily referring to the same embodiment, although the inventive concepts disclosed herein are intended to encompass all combinations and permutations including one or more features of the embodiments described.

In the present disclosure, a set of coordinates revealing the X, Y and Z directions are also shown in FIG. 1 and serve to provide a basis for identifying orientation of a feature or claim element throughout this disclosure. It should be known that other orientations are contemplated.

The term "fluid" as used herein refers to a liquid and/or gas that is configured to be passed through at least a portion of a sensor array. The fluid may be a sample, calibration reagent (e.g., fluid or gas), a wash fluid, or a quality control fluid.

The term "user", as used herein, is not limited to a human being, and may comprise, a computer, a server, a website, a processor, a network interface, a human, a user terminal, a virtual computer, combinations thereof, and the like, for example.

Referring to the Figures, and in particular to FIGS. 1-5, illustrated therein is an exemplary sensor array 10 having one or more optimization sensors 80 in accordance with the present disclosure. The sensor array 10 may be configured for analysis of one or more physical parameters and/or one or more chemical constituents of a volume of fluid within a flow path 48 of the sensor array 10. The fluid may be a liquid and/or gas composition. In some embodiments, the fluid may be a bodily fluid. It should be apparent to one skilled in the art that the concepts disclosed herein may be applicable to other industries, and further, that the fluid may be any liquid and/or gas composition not limited to a body. The one or more optimization sensors 80 may be configured to provide one or more performance parameters of the sensor array 10. Performance parameters may include data correlating and/or influencing health and/or performance of the sensor array 10. For example, performance parameters may include, but are not limited to, leakage indicators (e.g., fluid or analyte leakage as a result of bond failure), environmental indicators (e.g., heat, humidity, light, corrosion), combinations thereof, or the like. Generally, the optimization sensor 80 is positioned within the housing and outside of the flow path 48 of the sensor array 10 as described in further detail herein. Fluid outside of the flow path 48 of the sensor array 10 may, for example, include a sample (e.g., blood sample, urine sample), a calibration reagent (e.g., fluid or gas), a wash fluid, or a quality control fluid).

The sensor array 10 includes a sensor panel 14 having an upper surface 16 and a lower surface 18. In some embodiments, one or more analyte sensor 20 may be positioned on the lower surface 18. The sensor panel 14 may be fabricated from materials including, but not limited to ceramics, plastic, and/or the like. In some embodiments, one or more optimization sensor 80 may be on the lower surface 18 and/or integral to the sensor panel 14. Generally, the one or more optimization sensor 80 may be positioned within the sensor array 10 and outside of the flow path 48 of the sensor array 10.

The one or more optimization sensor 80 include, but are not limited to, one or more of thermistors, thermocouples, resistance temperature detectors (RTDs), flow sensors, pressure sensors, accelerometers, infrared sensors, light sensors, ultrasonic sensors, touch sensor, and/or other sensing element configured to provide sensing data related to the usability of the sensor array 10. For example, in some embodiments, one or more of the optimization sensor 80 may sense temperature, proximity, pressure of the surrounding environment, flow of fluid outside of the flow path 48 of the sensor array 10, humidity, corrosion, light, electrical capacity, combinations thereof, and the like. One or more optimization sensor 80 may be active sensor and/or passive sensor. One or more optimization sensor 80 may be photoelectric, thermoelectric, electrochemical, electromagnetic thermooptic, and/or the like. One or more optimization sensor 80 may be analog sensors or digital sensors.

In some embodiments, one or more optimization sensor 80 may include a temperature sensor (e.g., thermistor, thermocouple, resistance temperature device (RTD) temperature device) configured to sense the temperature (e.g., measure changes in temperature) outside of the flow path 48 of the sensor array 10. In some embodiments, one or more optimization sensor 80 may include a proximity sensor configured to detect presence of fluid outside of the flow path 48 of the sensor array 10. The proximity sensor may use one or more techniques including, but not limited to optical (e.g., infrared), ultrasonic, capacitive, and/or the like, to detect presence of the fluid outside of the flow path of the sensor array 10. In some embodiments, one or more optimization sensor 80 may include an ultrasonic sensor configured to measure distance and/or velocity of the fluid outside of the flow path 48 of the sensor array. In some embodiments, one or more optimization sensor 80 may include a light sensor configured sense wavelengths of light outside of the flow path 48 of the sensor array 10. In some embodiments, one or more optimization sensor 80 may include a humidity sensor configured to sense humidity outside of the flow path 48 of the sensor array 10.

In some embodiments, the one or more optimization sensor 80 may communicate with an optional analysis system 82 uni-laterally or bi-laterally. The analysis system 82 may utilize sensing data from the one or more optimization sensor 80 to determine usability and/or accuracy of the sensor array 10. The one or more optimization sensor 80 may transmit data to the analysis system 82 via a wired or wireless connection. The analysis system 82 may utilize one or more algorithm and data received from the one or more optimization sensor 80 to determine usability and/or accuracy of the sensor array 10. For example, in some embodiments, the analysis system 82 may utilize one or more algorithm and data received from the one or more optimization sensor 80 to determine whether to continue operation of the sensor array 10 or suspend operation of part or the entirety of the sensor array 10. The analysis system 82 may be configured to utilize techniques and/or algorithms known within the art (e.g., adaptive control, intelligent control, optimal control, and/or the like). In some embodiments, the analysis system 82 may provide one or more reports detailing data, usability of the sensor array 10, projected accuracy of the sensor array 10, and/or the like.

The analysis system 82 may comprise one or more processors capable of executing processor executable code and one or more non-transitory memory capable of storing processor executable code. The processor executable code cause the processor to receive data from the one or more optimization sensors 80; analyze the data received from the one or more optimization sensors 80; and, provide recommendations to a user regarding continued analysis of the sensor array 10 or discarding of the sensor array 10.

In some embodiments, the one or optimization sensor 80 may provide immediate feedback regarding usability and/or accuracy of the sensor array 10, and as such, the analysis system 82 may be optional for one or more of the optimization sensors 80.

In some embodiments, one or more of the optimization sensor 80 and/or analysis system 82 may include one or more physical indicators. Physical indicators may be visual, auditory, haptic and/or any type of physical indicator providing feedback to a user. For example, one or more physical indicators may include a visual indicator, such as an LED, or other type of light. In some embodiments, multiple visual indicators may provide information on a plurality of states or conditions or the sensor array 10. For example, a multi-color LED may be used to provide data on a plurality of states or conditions of the sensor array 10.

The one or more physical indicator of the optimization sensor 80 and/or analysis system 82 may provide feedback to the user of one or more performance parameters. For example, the one or more physical indicator of the optimization sensor 80 and/or analysis system 82 may provide feedback to the user if a pre-determined threshold is met by the optimization sensor 80. For example, if during transit, the one or more optimization sensor 80 exceeds or becomes out of range of a pre-determined temperature, pre-determined humidity, pre-determined corrosion level, is exposed to a pre-determined wavelength of light, combinations thereof and/or the like, the one or more optimization sensor 80 and/or analysis system 82 may provide a visual indicator to the user that the sensor array 10 may be considered void.

Referring again to FIGS. 1-5, one or more optimization sensor 80 may be positioned on the lower surface 18 and/or integral to the sensor panel 14. In some embodiments, a plurality of optimization sensors 80 may be positioned about and/or along the flow path 48 of the sensor array 10.

In some embodiments, the sensor array 10 may include an adhesive layer 24 having an upper surface 26 and a lower surface 28. The adhesive layer 24 may include a first longitudinal edge 30 and a second longitudinal edge 32. A fluid pathway 36 may span proximate the first longitudinal edge 30 and/or the second longitudinal edge 32. In some embodiments, one or more optimization sensor 80 may be positioned on the upper surface 26 and/or the lower surface 28 of the adhesive layer 24. In some embodiments, one or more optimization sensor 80 may be positioned integral to the adhesive layer 24. Positioning of the optimization sensor 80 on and/or integral to the adhesive layer 24 within the sensor array 10 may ensure that the optimization sensor 80 is outside of the flow path 48 of the sensor array 10.

In some embodiments, the upper surface 26 of the adhesive layer 24 may be adhesively secured to the lower surface 18 of the sensor panel 14. The lower surface 28 of the adhesive layer 24 may be secured to an inset bed 41 of a sensor cartridge base 40. In some embodiments, the adhesive layer 24 may be optional. In some embodiments, one or more optimization sensor 80 may be positioned within the inset bed 41 of the sensor cartridge base 40. In some embodiments, one or more optimization sensor 80 may be integral to the sensor cartridge base 40. Positioning and/or alignment of the optimization sensor 80 within the inset bed 41 and/or integral to the sensor cartridge base 40 may ensure that the optimization sensor 80 is outside of the flow path 48 of the sensor array 10.

The sensor cartridge base 40 may include a fluid inlet 42 and a fluid outlet 44. The flow path 48 may extend between the fluid inlet 42 and the fluid outlet 44. In some embodiments, the flow path 48 mirrors the shape and span of the contoured fluid pathway 36 of the adhesive layer 24.

Generally, a fluid 50 may be input at the fluid inlet 42. The flow path 48 is configured such that the fluid 50 traverses along the flow path 48 for contact with one or more analyte sensor 20 (see FIG. 4) before exiting at the fluid outlet 44. In some embodiments, one or more optimization sensor 80 may be configured to detect whether the fluid traverses in one or more areas outside of the flow path 48.

In some embodiments, volumetric capacity of the flow path 48 between the fluid inlet 42 and the fluid outlet 44 may be in the range of about 20 to 35 μl. For example, volumetric capacity of the flow path 48 may be 20 μl, 21μ, 22 μl, 23 μl, 24 μl, 25 μl, 26 μl, 27 μl, 28 μl, 29 μl, 30 μl, 31 μl, 32 μl, 33 μl, 34 μl, 35 μl, or ranges therein.

The sensor array 10 may utilize the sensor panel 14 having one or more analyte sensors 20 located on the lower surface 18. Accompanying each analyte sensors 20 may be one or more sensor contacts 54a-54n. The sensor contacts 54a-54n may be positioned on the lower surface 18 of the sensor panel 14 as shown in FIG. 1. The sensor contacts 54a-n may pass through the sensor panel 14 by vias such that the sensor contacts 54a-n are accessible from the upper surface 16. Thus, a portion of the sensor contacts 54a-n may be located on the upper surface 16 of the sensor panel 14. In some embodiments, the sensor contacts 54a-n may be laterally and/or oppositely disposed from one another across the flow path 48. Alternatively, the sensor contacts 54a-n may be located on the lower surface 18 of the sensor panel (as shown in FIG. 1).

Figures 2, 3, 4:
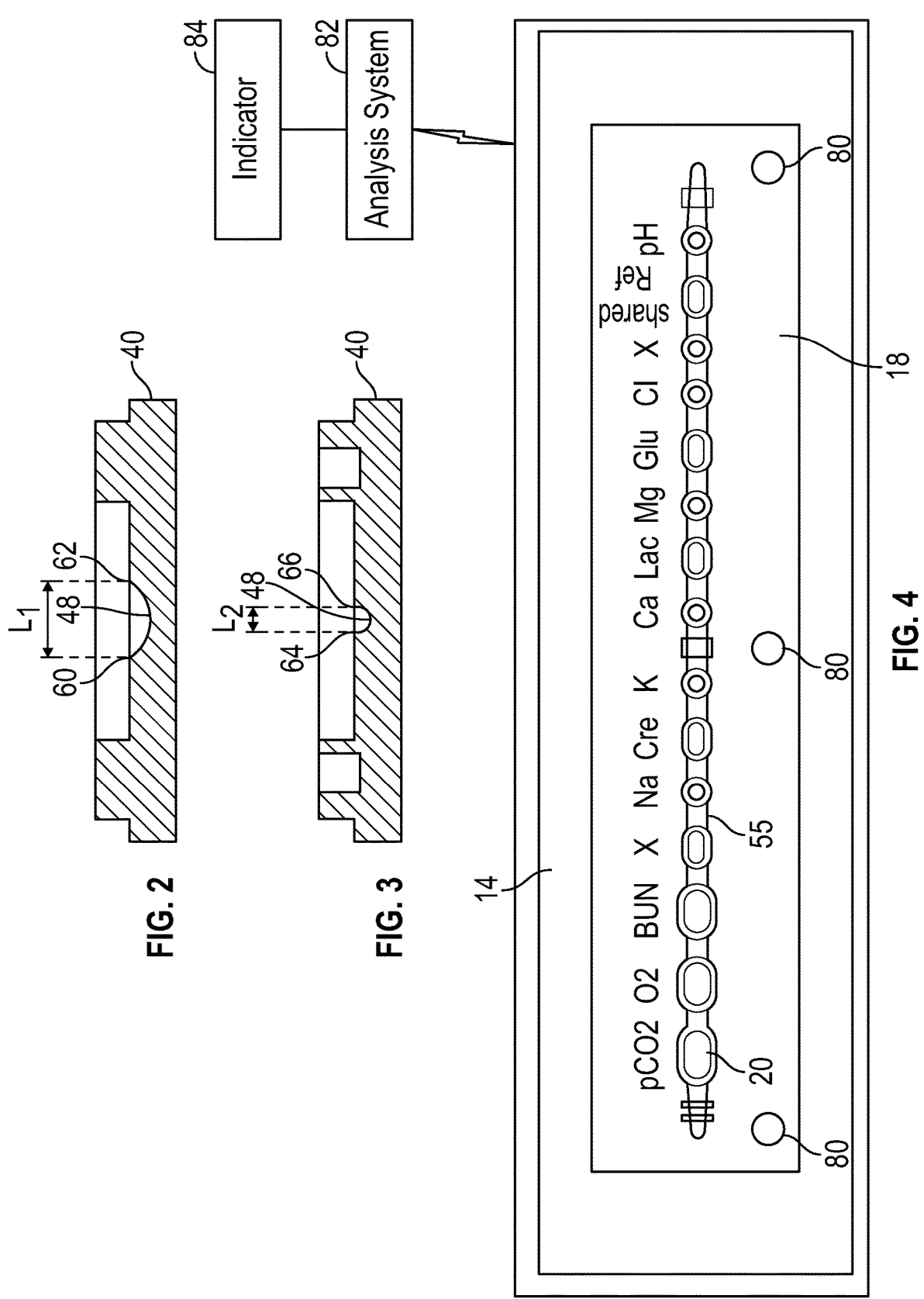

Referring to FIGS. 1, 4 and 5, in some embodiments, the sensor contacts 54a-n may be engaged by prepositioned leads (not shown) within the sensor cartridge assembly (not shown). In some embodiments, dimensions of the contoured flow path 48 may increase (e.g., Y and/or Z direction), in close proximity to an analyte sensor 20, and reduce (e.g., Y and/or direction), when transitioning between analyte sensors 20 forming an exemplary transition area 55. The exemplary transition area 55 may be narrowed between analyte sensors 20. In some embodiments, the exemplary transition area 55 may reduce need for fluid volume in order to perform the desired analysis of the fluid.

In some embodiments, dimension of the flow path 48 may increase in the Y direction, in close proximity to one of the analyte sensors 20 and reduces in Y direction, when transitioning between analyte sensors 20 while the dimension in the Z axis remains constant throughout the flow path.

In some embodiments, dimensions of the flow path 48 in the Z axis may increase and/or decease along with the dimensions in the Y axis. In some embodiments, dimensions of the flow path 48 may increase in the Z direction, in close proximity to an analyte sensor 20 and reduces in Z direction, when transitioning between analyte sensors while the dimension in the Y axis remains constant throughout the flow path. In some embodiments, the dimensions of the flow path in the Y axis may also increase and decease along with the dimensions in the Z axis.

FIG. 2 illustrates a sectional view of FIG. 1 taken at sectional line 2-2 of the sensor cartridge base 40 showing the flow path 48 at one of the analyte sensors 20. The cross-sectional configuration of the flow path 48 may be circular, square, triangular, hexagonal, serpentine, or any fanciful shape. The fluid pathway 36, and the lower surface 18 of fluid panel 14 adjacent to the fluid pathway may contribute to the flow path 48. With respect to the flow path 48 formed within the inset bed 41 of the sensor cartridge base 40, the flow path 48 may include a first upper edge 60 and a second upper edge 62. The first upper edge 60 and the second upper edge 62 may be positioned at the intersection of the walls of the flow path 48 and the inset bed 41 of the sensor cartridge base 40. In some embodiments, a length $L_1$ between the first upper edge 60 and the second upper edge 62 may be in the range of about 0.300 to 0.600 mm. Dimensions outside of the range are also contemplated by this disclosure.

FIG. 3 is another cross-sectional view taken at sectional line 3-3 of FIG. 1 of the sensor cartridge base 40 showing the flow path 48 illustrating an exemplary transition area 55. The flow path 48 includes a first upper edge 64 and a second upper edge 66. The first upper edge 64 and the second upper edge 66 are at the intersection of the walls of the flow path 48 and the inset bed 41 of the sensor cartridge base 40. In some embodiments, a length $L_2$ between the first upper edge

64 and the second upper edge 66 may be less than the length $L_1$, such as within the range of 0.100 mm to 0.250 mm and the depth of the contoured flow path 48 from the narrowest cross section length to the widest cross section length may be in the range of from 0.200 to 0.400 mm. Dimensions outside of the range are also contemplated by this disclosure.

The flow path 48 may oscillate between wider cross section length $L_1$ and narrower cross section length $L_2$ within the exemplary transition area 55 spanning along the length of the flow path 48. To that end, the flow path 48 may be elongated and have different cross-section length between each end. In some embodiments, cross-section length may be configured to minimize the amount and/or provide a suitable amount of fluid needed to provide an accurate and/or precise result via the analyte sensors 20. In some embodiments, the flow path 48 may maintain a sufficiently unrestricted fluidic connection in order to sustain fluid pressure to facilitate conveyance through the sensor array 10.

Though the term "beneath" may be used in describing the orientation of the flow path 48 relative to location of one or more analyte sensor 20 and one or more optimization sensor 80, this disclosure contemplates that the flow path 48 may be located above the analyte sensors 20 and/or above the optimization sensor 80 and the term "beneath" should not be considered limiting.

In some embodiments, cross section length of the flow path 48 may comparatively widen when in proximity to one or more analyte sensor 20. For example, in some embodiments, the one or more analyte sensor 20 may need to be provided with a pre-determined fluid volume and/or minimum surface area of contact for accuracy and/or precision. In some embodiments, cross section length of the flow path 48 may be comparatively reduced wherein no analyte sensors 20 are within in the flow path 48, for example.

Referring to FIG. 4, the sensor array 10 may be configured to analyze one or more constituent concentrations and/or fluid parameters. For example, the sensor array 10 may include analyte sensors 20 configured to measure, for example, pCO2, O2, BUN, Na, Cre, K, Ca, Lac, Mg, Glu, Cl, pH, combinations thereof, or the like.

Figure 5A:
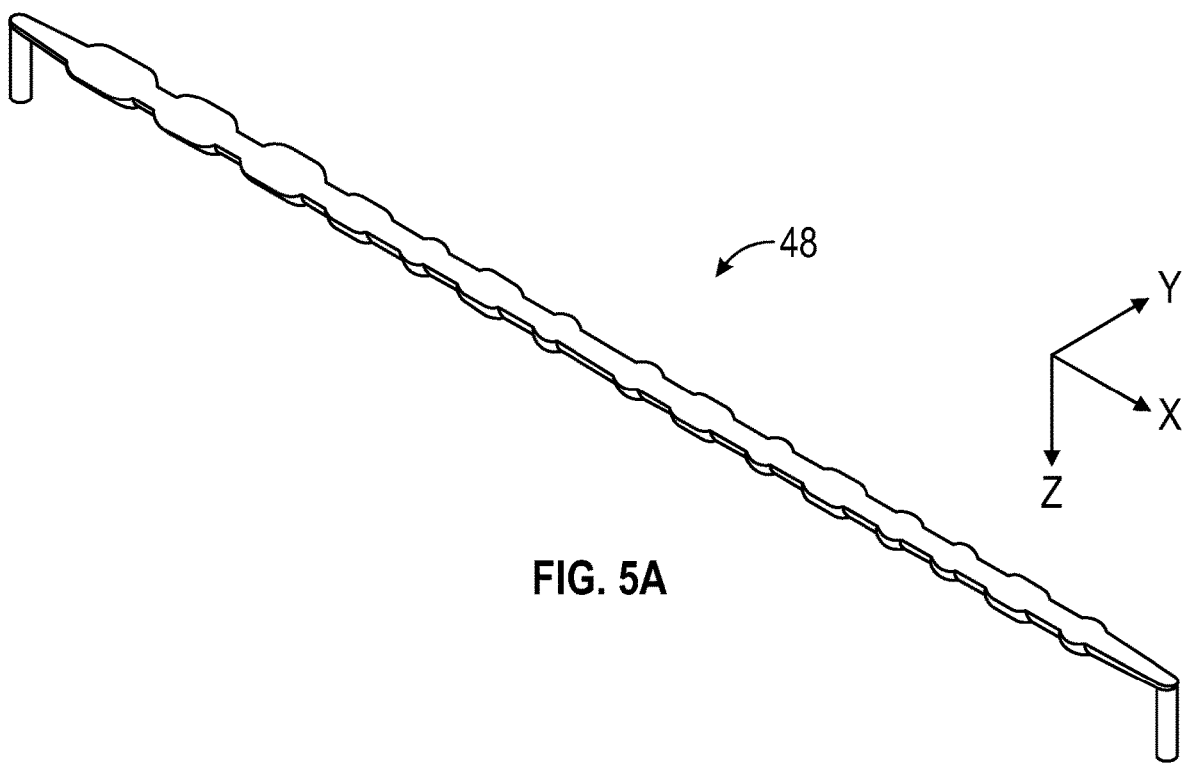

FIG. 5A illustrates a perspective view of an exemplary embodiments of the fluid appear traversing, in the X direction, through the flow path 48 of the sensor cartridge base 40. The length of the cross section of the flow path 48 may increase in the Y and/or Z directions wherein proximity to the analyte sensors 20, for example. The length of the cross section of the flow path 48 may comparatively decrease in dimension in the Y and/or Z directions, when traversing between one or more analyte sensors 20.

Figure 5B:
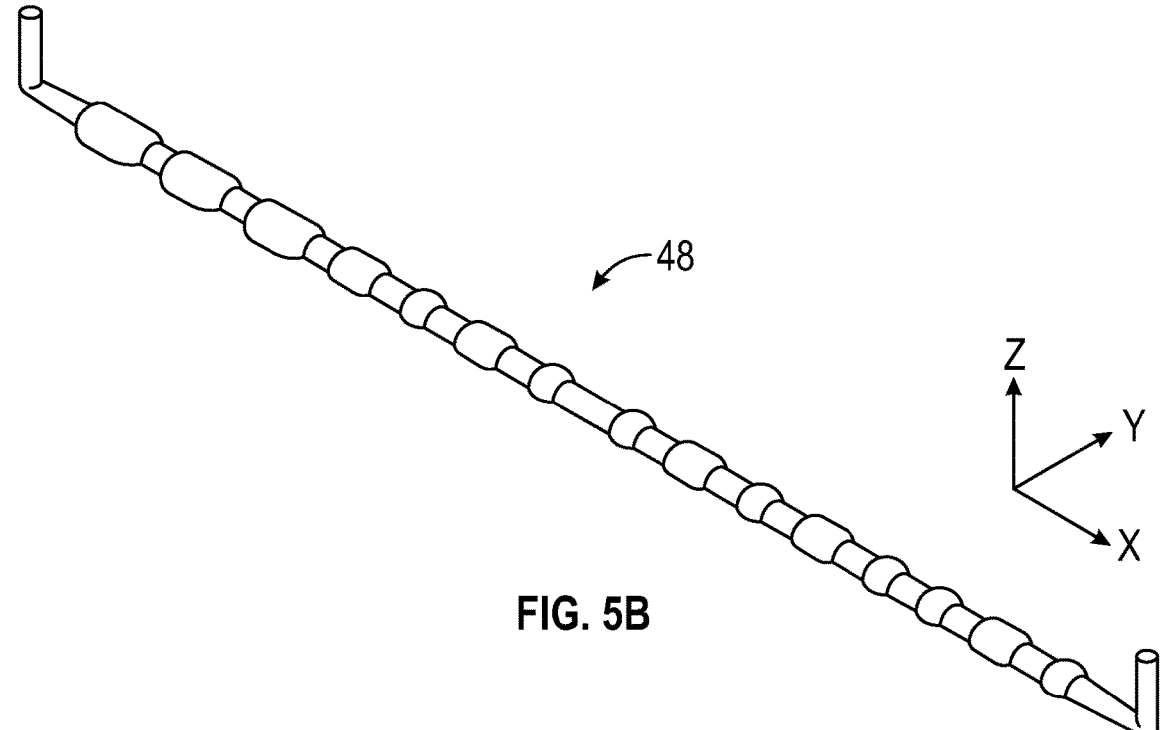

FIG. 5B illustrates another perspective view of the flow path 48 illustrating how length of the cross section of the flow path 48 may increase in the Y and/or Z directions and comparatively decrease in the Y and/or Z directions. For example, where there are no analyte sensor 20 within the flow path 48 at a particular location, there are no sensor surface area requirements thereby allowing the length of the cross-section of the flow path 48 to decrease dimensionally as detailed herein.

The following exemplary method of using the sensor array 10 is related to a blood draw. It is contemplated that other fluid, liquid and/or gas may be used and blood is not limiting within the disclosure. In operation, the one or more optimization sensors 80 may be configured to provide one or more performance parameters of the sensor array 10. Performance parameters may include data correlating and/or influencing health and/or performance of the sensor array 10. For example, performance parameters may include, but are not limited to, health of the sensor array 10 (e.g., fluid or analyte leakage as a result of bond failure), environmental data (e.g., heat, humidity, light, corrosion), combinations thereof, or the like. In some embodiments, data obtained from the one or more optimization sensor 80 by a processor of the analysis system 82 may be interpreted to provide a first usability report via one or more physical indicators 84. The physical indicator 84 may provide visual, haptic, or auditory feedback to a user, such as a human operator of the analysis system 82. For example, a visual feedback may be provided by an LED, a series of LEDs, a display screen, a print-out or a flashing light that serves to notify a user, e.g., a human, of the potential performance of the sensor array 10. Haptic feedback can be provided in the form of vibration, and can be implemented by a solenoid or piezoelectric device configured to cause vibration or movement upon receipt of a signal. Auditory feedback can be provided by a speaker. The usability report may be, for example, an activated red LED indicating that expected performance of the sensor array 10 is low due to the sensor array 10 being stored in a temperature outside of a pre-determined suitable range thus rendering the sensor array 10 unusable and/or inaccurate. The one or more optimization sensor 80 may be coupled to a source of electricity to permit a sensor of the optimization sensor 80 to collect data over a time period. The optimization sensor 80 may also include a processor and at least one non-transitory computer readable medium. The sensor may be configured to obtain sensor data, and supply such sensor data to the processor (e.g., via an analog to digital converter) for interpretation with a predetermined algorithm and/or storage of the sensor data or interpretation data derived from the sensor data within the non-transitory computer readable medium.

In some embodiments, the one or more optimization sensor 80 may provide sensor data or interpretation data that the analysis system 82 interprets to provide a second usability report, in lieu of, or in addition to the first usability report. The second usability report may be provided subsequent to fluid entering the flow path 48 of the sensor array 10. To that end, fluid may be obtained and/or provided to the flow path 48 of the sensor array 10. For example, the fluid may be withdrawn from a patient generally via a syringe or other standard blood draw technique. As previously detailed, the blood draw is very minimal in volume, generally no greater than 30 µl. The fluid 50 is then aspirated into the fluid inlet 42. Upon entering the fluid inlet 42, the fluid 50 traverses along the flow path 48. Traversing along the flow path 48 places the fluid beneath one or more analyte sensors 20 configured to detect a measureable outcome (e.g., change in voltage, amperage).

The different lengths of cross section (Y and/or Z direction) within the flow path 48 (e.g., diverging and converging of the flow path) may minimize volume of fluid required for proper operation of the sensor array 10 (.e.g., accurate and/or precise measurements). Change in voltage or amperage at one or more analyte sensors 20 (ion-selective electrodes) may be relayed to the sensor contacts 54 mounted to the sensor panel 14. The change in voltage, or amperage, detected at the analyte sensors 20 may be transmitted from the sensor contacts 54 to the analyzer system 82 or a separate analyzer (not shown). The analyzer system 82 and/or separate analyzer, using a suitable algorithm determines the concentrations of the fluid (blood) constituents and other parameters such as blood gases.

Fluid outside of the flow path 48 of the sensor array 10 (e.g., due to leak, insufficient bonding) may be detected by the one or more optimization sensor 80. In some embodiments, data provided by the one or more optimization sensor 80 may be provided to the analyzer system 82. The analyzer system 82 may analyze data received from the one or more optimization sensor 80 and determine usability of the sensor array 10. The analyzer system 82 may provide the second usability report detailing usability of the sensor array 10 by outputting one or more signals indicative of the performance of the sensor array 10 to the indicator(s) 84. In some embodiments, the one or more physical indicators 84 may provide feedback regarding the second usability report. For example, one or more LED may provide an indication that fluid is outside of the flow path 48 of the sensor array 10 and the sensor array 10 is rendered inaccurate. The user may discard the sensor array 10, discard data obtained via the sensor array 10, or continue analysis of the fluid within the flow path 48 of the sensor array 10.

Figure 6:
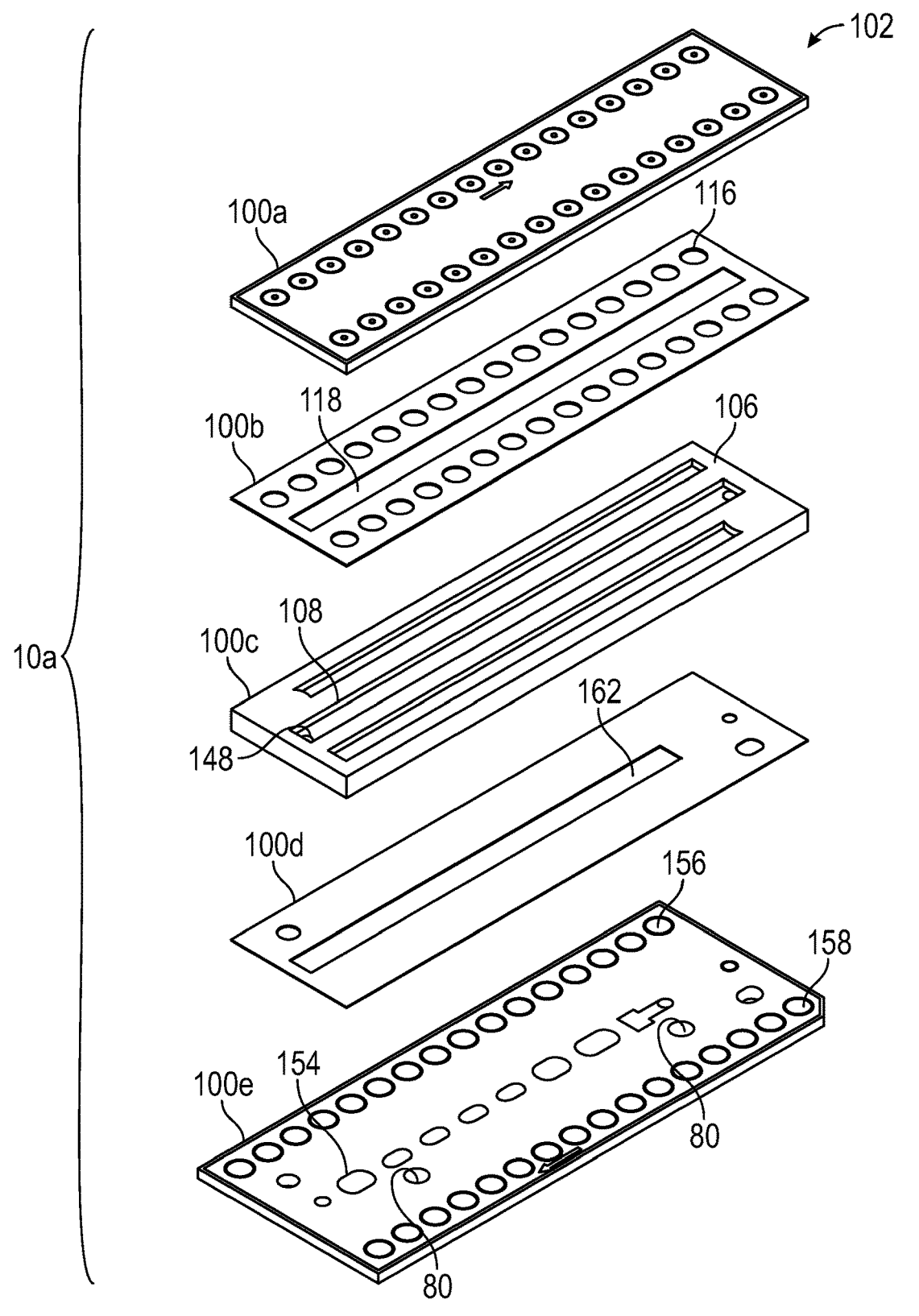
FIGS. 6-8 illustrate another exemplary embodiment of a sensor array having one or more optimization sensors in accordance with the present disclosure.
Figure 7:
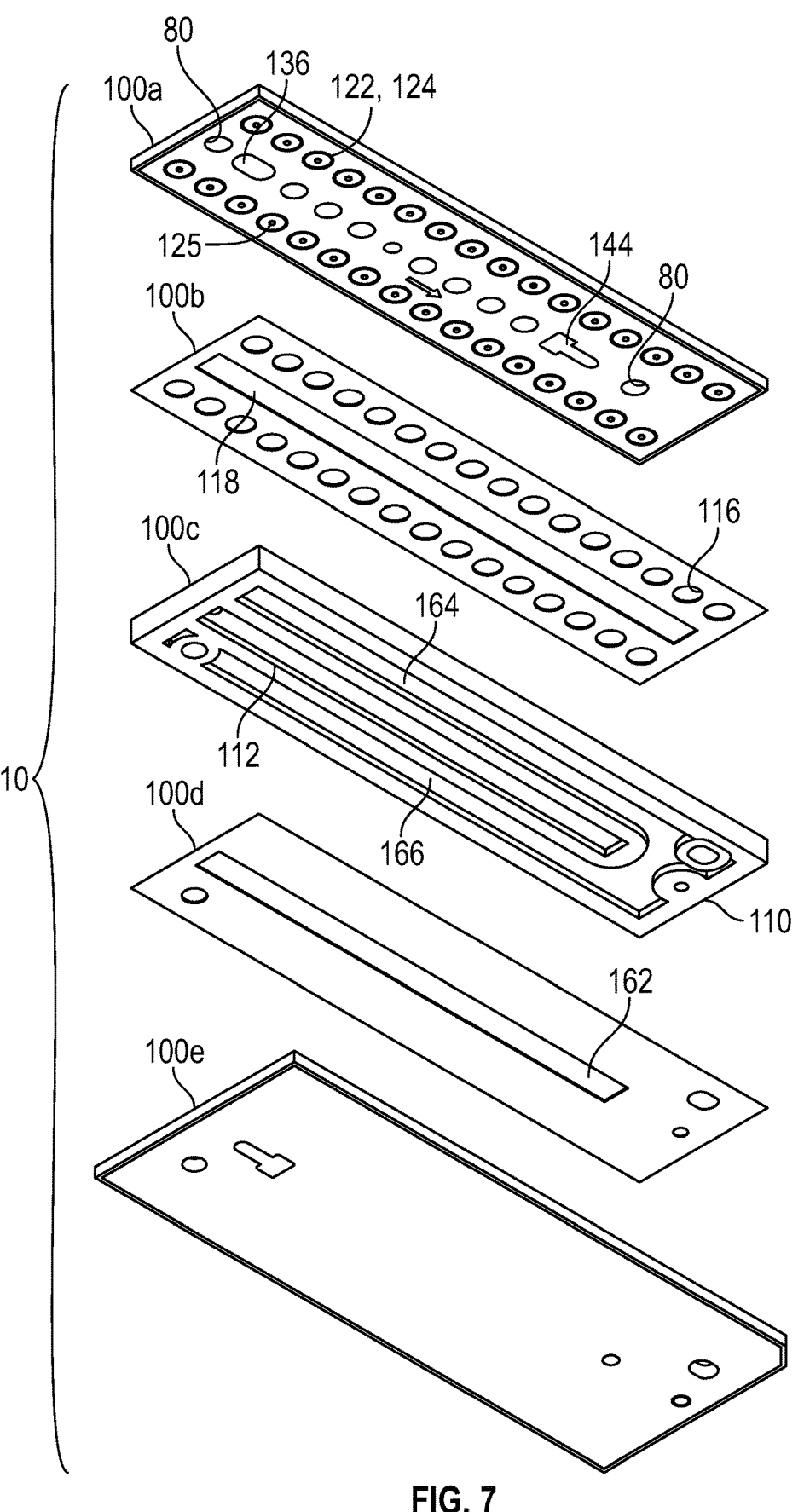
Figure 8:
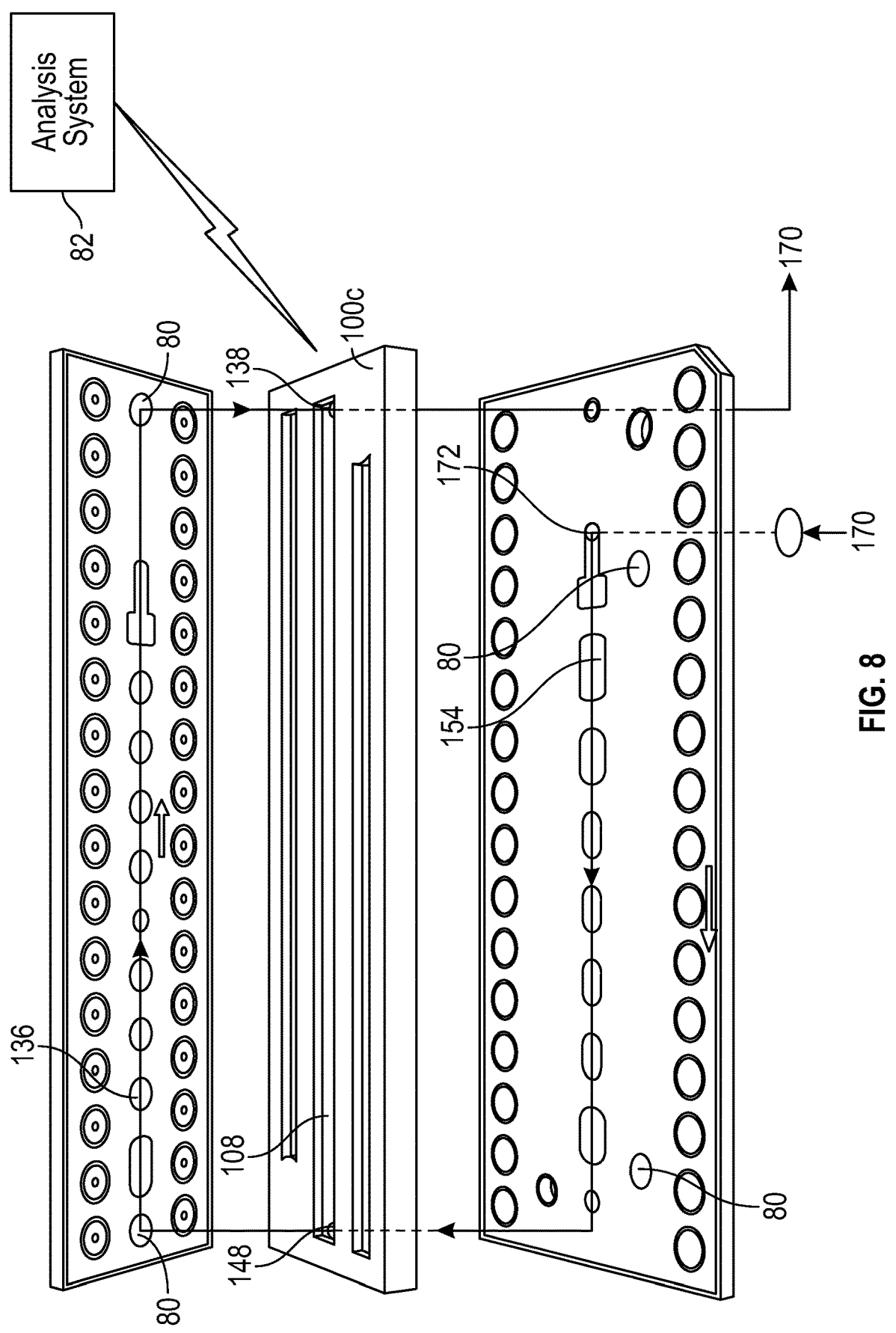

FIGS. 6-8 illustrate another embodiment of an exemplary sensor array 10a having one or more optimization sensor(s) 80 in accordance with the present disclosure. The sensor array 10a may be configured for analysis of one or more physical parameters and/or one or more chemical constituents of a volume of fluid. The fluid may be a liquid and/or gas composition. In some embodiments, the fluid may be a bodily fluid. The sensor array 10a is a stacked sensor array configured to receive and/or test one or more fluid. The one or more optimization sensors 80 may be configured to provide data correlating and/or influencing health and/or performance of the sensor array 10a in a similar manner as discussed above with respect to the sensor array 10. Generally, the one or more optimization sensor 80 may be positioned outside of the flow path of the sensor array 10a as described in further detail herein.

Referring to FIG. 6, the stacked sensor array 10a may include a plurality of stacked layers 100a-100e. The layer 100a (referred to herein interchangeably as "first sensor layer") may include one or more potentiometric sensors, one or more amperometric sensors, combinations thereof, or the like. One or more optimization sensor 80 may be positioned on one or more of the stacked layers 100a-100e.

The layer 100a may serve as a separation panel and include a potentiometric chip 102. The layer 100c (referred to herein interchangeably as "separation panel"), includes an upper surface 106 with an upper fluid channel 108 for passage of the fluid. The layer 100c may be formed of one or more material configured to reduce unintended electromagnetic cross-talk between one or more sensors located on the oppositely disposed chip thereby improving the accuracy, precision and/or reliability of data obtained by the sensor. In some embodiments, one or more optimization sensor 80 may be positioned on the upper surface 106 outside of the upper fluid channel 108.

Layer 100b may be an optional upper gasket disposed between the potentiometric chip 102 and the layer 100c (i.e., separation panel). The layer 100b (referred to herein interchangeably as "upper gasket") may be configured to seal the layer 100c against leakage of the fluid. In some embodiments, the layer 100b may be formed of one or more flexible fluid resistant material capable of forming a seal against leakage. The layer 100b (i.e., upper gasket layer) may include a series of perforations 116 located on each side of a centralized cutout 118. The perforations 116 in the layer 100b may provide an opening for the lower protruding surface 122 of the analyte sensor contact points 124, 125.

Referring to FIGS. 6 and 7, the layer 100a (i.e., first sensor layer) may include one or more analyte sensor 136. The one or more analyte sensor 136 may be positioned adjacent to the upper fluid channel 108. Each analyte sensor 136 may include two or more analyte sensor contact points 124, 125 for connecting the analyte sensor 136 to the analyzer system 82 and/or a separate analyzer (not shown). In some embodiments, one or more optimization sensor 80 may be positioned on the layer 100*a* and spaced from the upper fluid channel 108.

The upper fluid channel 108 (i.e., flow path) of the layer 100*c* (i.e., separation layer) may serves as a conduit for the fluid being measured by the analyte sensor 136 (i.e., upper analyte sensor). The upper fluid channel 108 may be generally linear in configuration. In some embodiments, the upper fluid channel 108 may be rectangular. Other cross-sectional configurations, such as arcuate, serpentine and fanciful are also contemplated by this disclosure.

Layer 100*e* (referred to herein interchangeably as "second sensor layer") is disposed beneath the layer 100*c* (i.e., separation layer). The layer 100*e* may include one or more analyte sensors 154 (e.g., amperometric sensors, one or more potentiometric sensors, combinations thereof, or the like). Additionally, in some embodiments, the layer 100*e* may include one or more optimization sensor 80.

As shown in FIGS. 6 and 7, the layer 100*e* (i.e., second sensor layer) includes one or more analyte sensor 154 disposed adjacent the lower fluid channel 112 and two electrical contact points 156 and 158, for connecting the analyte sensor 154 with an analyzer (not shown). The one or more optimization sensor 80 may be positioned at a distance from the lower fluid channel 112. As shown in FIG. 7, positioned above the layer 100*e* (i.e., second sensor layer) is the layer 100*c* (i.e., separation panel). The layer 100*c* (i.e., separation layer) includes a lower surface 110 with the lower fluid channel 112 for passage of the sample fluid. The lower surface 110 with a lower fluid channel 112 is in fluid communication with the upper fluid channel 108. As the one or more optimization sensor 80 are outside of the flow path (i.e., upper fluid channel 108 and/or lower fluid channel 112), the one or more optimization sensor 80 may be positioned at a distance from the lower fluid channel 112 and/or lower fluid channel 112.

Optionally disposed between the layer 100*e* and the layer 100*c* is a layer 100*d* (referred to herein interchangeably as "lower gasket layer"). The layer 100*d* may be configured to seal the layer 100*c* from leakage of the sample fluid. The layer 100*d* may be formed of one or more flexible fluid resistant material configured to form a seal against leakage. The layer 100*d* (i.e., lower gasket layer) may include a cutout area 162 that coincides with the location and configuration of the lower fluid channel 112. In some embodiments, one or more optimization sensor 80 may be positioned on and/or integral to the layer 100*d* at a distance from the cutout area 162 that coincides with the location and configuration of the lower fluid channel 112.

As shown in FIG. 7, the layer 100*c* may include one or more channels (e.g., a first channel 164 and 166 a second channel) straddling the lower fluid channel 112. In some embodiments, channels 164 and 166 may be optional. Channels 164 and 166 may be configure to facilitate fabrication of the layer 100*c* (i.e., separation panel) by inhibiting warping resulting from excess molded material. In some embodiments, one or more optimization sensor 80 may be positioned on and/or integral to the layer 100*e*. In some embodiments, one or more optimization sensor 80 may be configured to sense warping resulting from excess molded material. For example, the optimization sensor 80 may be a strain gauge whose resistance varies with applied force to convert force, pressure, tension, weight, or the like into a change in electrical resistance which can then be measured. The layer 100*e* (i.e., second sensor layer) may include one or more analyte sensor 154. Each analyte sensor 154 includes two or more electrical contact points (e.g., a first electrical contact point 156 and a second electrical contact point 158) for connecting each analyte sensor 154 with the analyzer system 82 and/or a separate analyzer (not shown).

The lower fluid channel 112 may be configured as a conduit for the fluid being analyzed by one or more analyte sensor 154 (i.e. lower analyte sensor). The lower fluid channel 112 may be narrow and generally linear in configuration. In some embodiments, the lower fluid channel 112 (i.e., flow path) may be non-linear, serpentine, and/or any fanciful shape.

The following exemplary method of using the sensor array 10*a* is related to a blood draw. It is contemplated that other fluid, liquid and/or gas may be used and blood is not limiting within the disclosure. In operation, the one or more optimization sensor 80 may provide data to the analysis system 82 that can be used to provide a first usability report of the one or more performance parameters via the one or more physical indicators 84. The usability report may be, for example, an activated red LED indicating that the sensor array 10*a* was stored in corrosive conditions outside of a pre-determined suitable range thus rendering the sensor array 10*a* unusable and/or inaccurate.

In some embodiments, the one or more optimization sensor 80 may provide data to the analysis system 82 that can be used to provide a second usability report, in lieu of, or in addition to the first usability report. The second usability report may be provided subsequent to fluid entering of the sensor array 10*a*. To that end, fluid 170 undergoing analysis enters the lower fluid channel 112 via opening 172. The fluid 170 then travels along the lower fluid channel 112 (i.e., flow path) providing access to one or more analyte sensors 154. The fluid 170 then traverses through an opening 148 in the layer 100*c* (i.e., separation panel) prior to entering the upper fluid channel 108 (i.e., flow path). After entering the upper fluid channel 108, the fluid 170 traverses beneath one or more analyte sensor 136 prior to transiting through the exit opening 138 in the layer 100*c* (i.e., separation panel).

Fluid outside of the of flow path (i.e., upper fluid channel 108 and/or lower fluid channel 112) of the sensor array 10*a* (e.g., due to leak, insufficient bonding) may be detected by the one or more optimization sensor 80. In some embodiments, data provided by the one or more optimization sensor 80 may be provided to the analyzer system 82. The analyzer system 82 may analyze data received from the one or more optimization sensor 80 and determine usability of the sensor array 10*a*. The analyzer system 82 may provide the second usability report to the one or more physical indicators 84 detailing usability of the sensor array 10*a*. In some embodiments, one or more physical indicators 84 may provide feedback regarding the one or more performance parameters in the second usability report. For example, one or more LED may provide an indication that fluid is outside of the flow path (i.e., upper fluid channel 108 and/or lower fluid channel 112) of the sensor array 10*a* and the sensor array 10*a* is rendered inaccurate. The user may discard the sensor array 10*a*, discard data obtained via the sensor array 10*a*, or continue analysis of the fluid within the flow path (i.e., upper fluid channel and/or lower fluid channel 112) of the sensor array 10*a*.

Figures 9, 10:
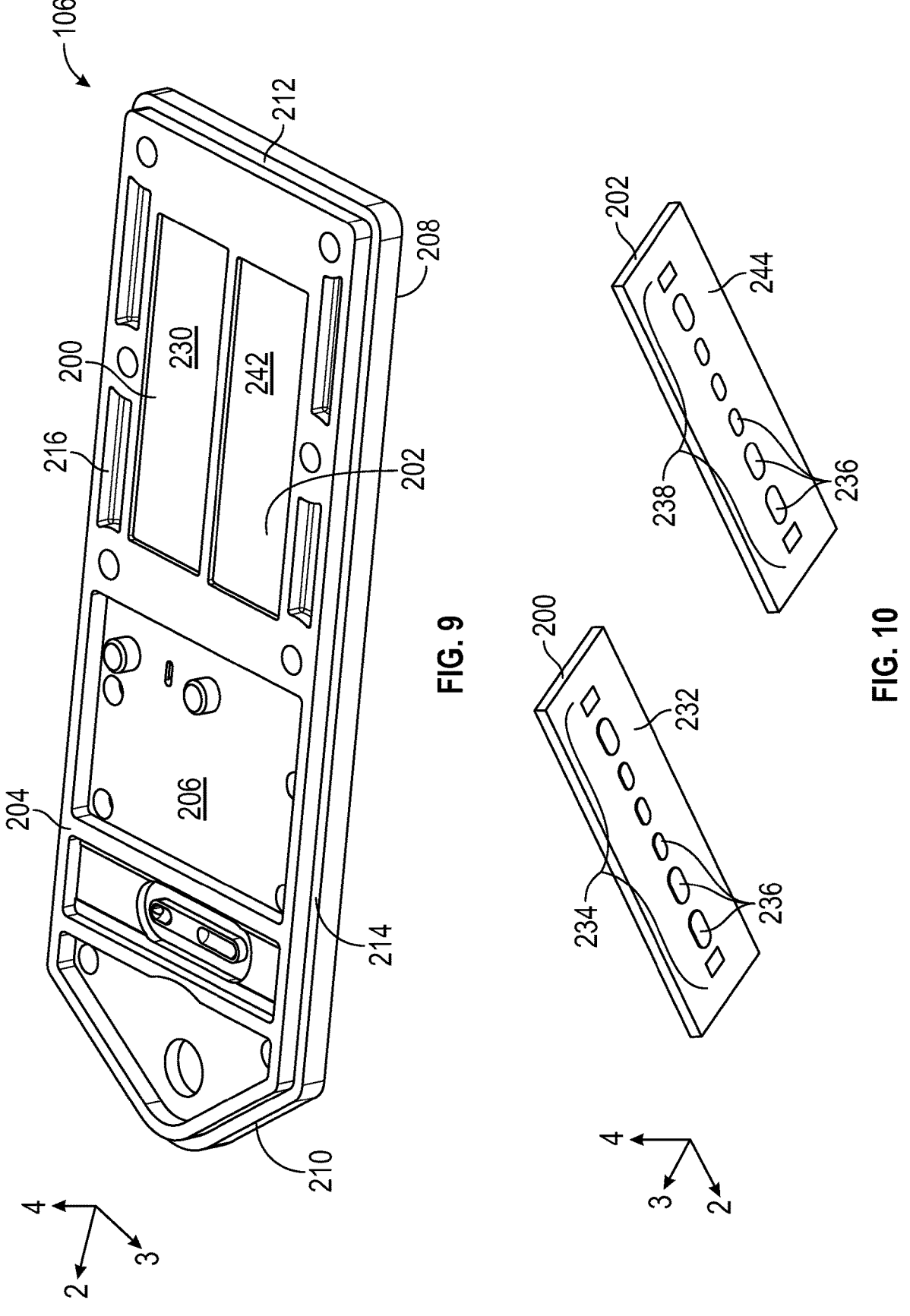
FIGS. 9-11 illustrate another exemplary embodiment of a sensor array having one or more optimization sensors in accordance with the present disclosure.
Figure 11:
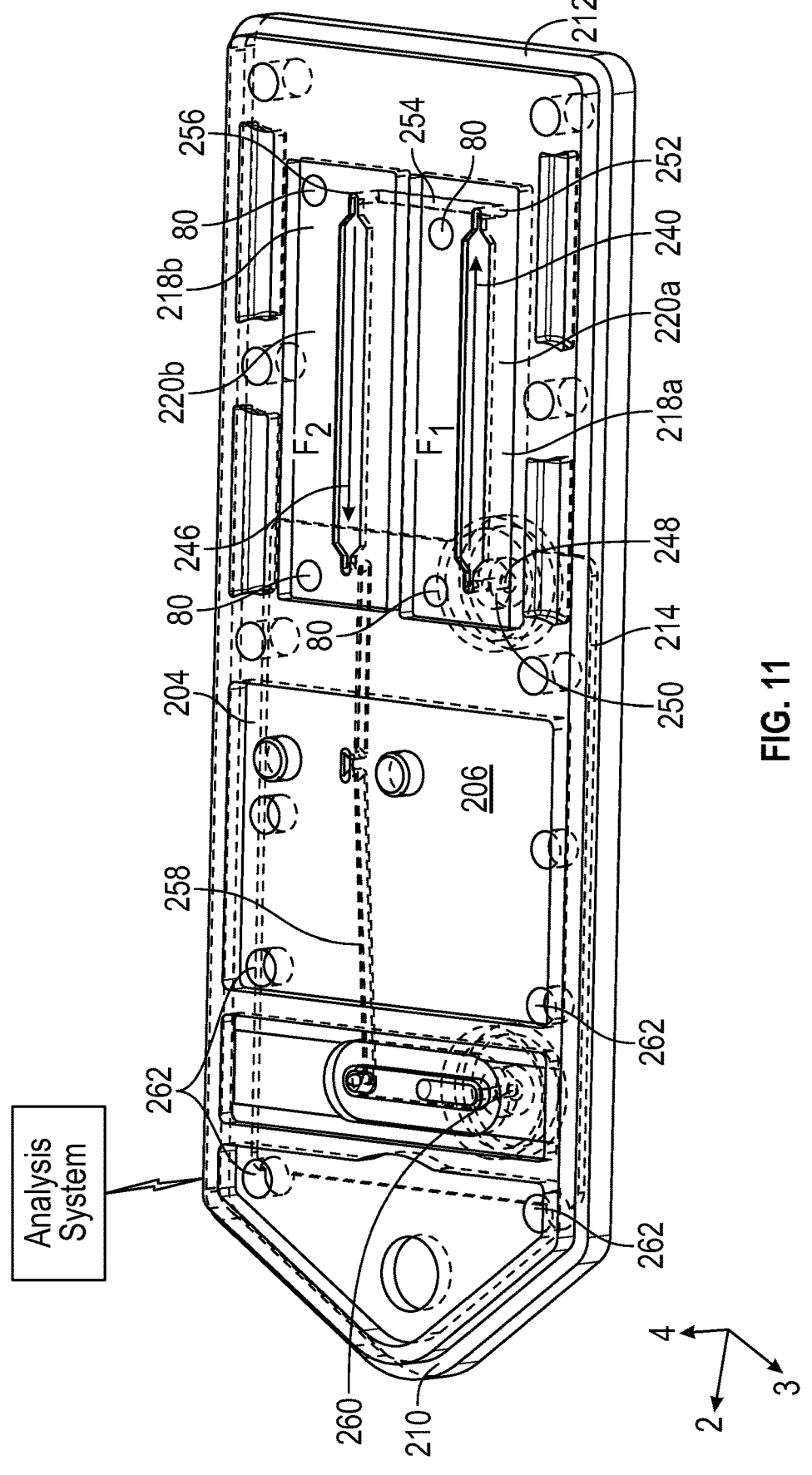

FIGS. 9-11 illustrate another embodiment of an exemplary sensor array 10*b* having one or more optimization sensors 80. The sensor array 10*b* may be configured for analysis of one or more physical parameters and/or one or more chemical constituents of a volume of fluid. The fluid may be a liquid and/or gas composition. In some embodiments, the fluid may be a bodily fluid. The one or more optimization sensors 80 may be configured to provide data correlating and/or influencing health and/or performance of the sensor array 10b. Generally, the one or more optimization sensor 80 may be positioned outside of the flow path of the sensor array 10b as described in further detail herein.

Referring to FIG. 9, the sensor array 10b includes a first sensor substrate 200, a second sensor substrate 202, and a base 204 configured to receive the first sensor substrate 200 and the second sensor substrates 202. The base 204 may define a plurality of fluidic passageways for receiving the sample fluid, as will be discussed further below. One or more optimization sensor 80 may be positioned outside of the fluidic passageways.

The base 204 is configured to be incorporated into a sample analysis system (not shown) for testing, analyzing, and displaying various aspects of the sample fluid. Generally, the base 204 may be configured to hold the sensor substrates in an offset configuration with respect to each other. As shown, the base 204 has a first surface 206, a second surface 208 opposite the first surface 206 along the vertical direction 4, a first end 210, a second end 212 opposite the first end 210 along the longitudinal direction 2, a first side 214, and a second side 216 opposite the first side 214 along the lateral direction 3.

The base 204 may define a substantially rectangular prism shaped body with the first end 210 having a forward-facing apex. However, the base 204 can define other shapes including spherical or any fanciful shape. For instance, the base 204 can be square, rectangular, oval, or have any other shape that facilitates placement and use with a sample analysis systems.

The base 204 may include a plurality of recesses for holding the first sensor substrate 200 and the second sensor substrate 202. The base 204 may include a first recess 218a that extends from the first surface 206 into the base 204 and terminates at a first inner surface 220a before the second surface 208. The first recess 218a may be configured to at least partially receive the first sensor substrate 200. The base 204 may include a second recess 218b that extends from the first surface 206 into the base 204 and terminates at a second inner surface 220b before the second surface 208. The second recess 218b may at least partially (or completely) receive the second sensor substrate 202. In some embodiments, one or more optimization sensor 80 may be positioned within the first recess 218a and/or the second recess 218b.

In some embodiments, the first recess 218a and the second recess 218b may be spaced apart along the lateral direction 3. The first recess 218a and second recesses 218b may also be substantially aligned along the lateral direction 3. In some embodiments, either of the first recess 218a and the second recesses 218b may be positioned elsewhere along the first surface 206 of the base 204. Each of the first recess 218a and second recesses 218b are illustrated as substantially rectangular in shape, though this may differ according to the shape of the particular sensor substrate that will be disposed within the first recess 218a and/or the second recess 218b. Each of the first recess 218a and the second recess 218b may be sized such that surface of the first sensor substrate 200 and the second sensor substrates 202 may be configured to be aligned with the first surface 206 of the base

204 when the first sensor substrate 200 and the second sensor substrate 202 are disposed within the first recess 218a and the second recess 218b.

Referring to FIG. 10, the first sensor substrate 200 and the second sensor substrate 202 each hold a plurality of sensors for testing a particular attribute of a fluid. The first sensor substrate 200 defines a first substrate surface 230 and a second substrate surface 232 opposite the first substrate surface 230 along the vertical direction 4. The first sensor substrate 200 is illustrated as a rectangular prism, though other shapes are contemplated. Though each of the first substrate surface 230 and the second substrate surface 232 is depicted as being substantially planar, the first substrate surface 230 and/or the second substrate surface may be alternatively shaped as desired. The first sensor substrate 200 may be configured as a first set 234 of sensors 236 disposed on the second substrate surface 232. The first set 234 of sensors 236 may include eight separate and distinct sensors. Each sensor 236 may be aligned on the first sensor substrate 200 along the longitudinal direction 2. However, the first set 234 of sensors 236 may include any number of sensors. Arrangement of a first set 234 of sensors 236 may generally align with shape of a first flow path 240, described in further detail below.

Any of the sensors 236 may be a potentiometric sensor for measuring a property of the sample fluid. Alternatively, the sensors 236 can be other types of sensors, such as amperometric, conductometric, thermometric, optical, piezoelectric sensors, or combinations thereof.

The second sensor substrate 202 defines a first substrate surface 242 and a second substrate surface 244 opposite the first substrate surface 242 along the vertical direction 4. As shown, the second sensor substrate 202 is depicted as defining a rectangular prism, though other shapes are contemplated. Though each of the first substrate surface 242 and the second substrate surface 244 is depicted as being substantially planar, both of the first substrate surface 242 and the second substrate surface may be alternatively shaped as desired. The second sensor substrate 202 may include second set 238 of sensors 236 disposed on the second substrate surface 244. The second set 238 of sensors 236 may include eight sensors, for example. Each sensor 236 may be aligned on the second sensor substrate 202 along the longitudinal direction 2. It is contemplated the second set 238 of sensors 236 may include more or less than eight sensors.

The arrangement of the second set 238 of sensors 236 may generally align with the shape of the second flow path 246, described in further detail herein. It is contemplated the second set 238 of sensors 236 may be arranged differently than what is explicitly shown. Any of the sensors 236 may be a potentiometric sensor. Alternatively, the sensors 236 may be other types of sensors. For instance, the sensors 236 may be amperometric, conductometric, thermometric, optical, piezoelectric sensors, and combinations thereof.

Although the sensors 236 of the first set 234 and the second set 238 are depicted as being substantially the same, the sensors 236 within each of the first set 234 and the second set 238 may define different types, arrangements, or numbers of sensors. For example, the first set 234 may include potentiometric sensors and the second set 238 may include a type other than potentiometric.

As illustrated in FIG. 11, one or more optimization sensor 80 may be positioned on and/or integral to the first sensor substrate 200 and/or the second sensor substrate 202. Each of the first sensor substrate 200 and the second sensor substrates 202 may be formed of one or more materials designed to hold the sensors. The first sensor substrate 200 and/or the second sensor substrate 202 may be formed using a variety of processes and materials that are known to a person of ordinary skill in the art. For example, the first sensor substrate 200 and/or the second sensor substrates 202 may be flexible or rigid and may be constructed using, for example, polymer, standard PCB, flex PCB, PET, PI, ceramic, glass, etc.

In some embodiments, after the first sensor substrate 200 and the second sensor substrate 202 are formed, the first set 234 of sensors 236 and the second set 238 of sensors may be attached to the first sensor substrate 200 and/or the second sensor substrate 202. The first sensor substrate 200 may then be attached to the base 204 in the first recess 218*a* with an adhesive. Likewise, the second sensor substrate 202 may be attached to the base 204 in the second recess 218*b* with an adhesive.

The first sensor substrate 200 and the second sensor substrates 202 may be positioned substantially parallel to each other when attached to the base 204. In this configuration, the first sensor substrate 200 and the second sensor substrate 202 may be spaced apart along the lateral direction 3, but aligned along the lateral direction 3, such that no portion of the first sensor substrate 200 overlies a portion of the second sensor substrate 202. Additionally, the first sensor substrate 200 and the second sensor substrate 202 may be vertically aligned, though some vertical offset is contemplated.

Referring to FIGS. 9 and 11, the base 204 can define a plurality of passages for transporting the sample fluid through the sensor array 10*b*. The base 204 and passages contained therein can be formed through injection molding, though other procedures are also contemplated. The base 204 can include an inlet 248 located on the second surface 208 for receiving the sample fluid from another portion of the sample analysis system (not shown). As depicted, the inlet 248 can be located along the second surface 208 at a position that overlies a portion of the first sensor substrate 200 and the first recess 218*a*, such that the flow length of the sample fluid from the inlet 248 to the first sensor substrate 200 is minimized. However, it should be understood that the inlet 248 could be located elsewhere along the second surface 208, or alternatively along the first surface 206.

A first inlet passage 250 can extend substantially vertically from the inlet 248 to the first flow path 240, which is the portion of the fluid channel in which the first set 234 of sensors 236 are exposed to the sample fluid. The first flow path 240 is substantially open to the first recess 218*a* and can extend substantially along the longitudinal direction 2. The first flow path 240 can also extend into the base 204 from the first recess 218*a*. For example, the first flow path 240 can extend from the first inner surface 220*a* towards the second surface 208 and terminate before the second surface 208. The first flow path 240 can define a length along the longitudinal direction 2 that is less than a length of the first recess 218*a* along the longitudinal direction 2. Additionally or alternatively, the first flow path 240 can define a width along the lateral direction 3 that is less than a width of the first recess 218*a* along the lateral direction 3. In this configuration, when the sample fluid flows through the first flow path 240, the sample fluid flows along a first flow direction F1 that is substantially parallel to the longitudinal direction 2. However, the first flow path 240 and the first flow direction F1 are angularly offset from the longitudinal direction 2.

The first flow path 240 is partially defined by the base 204 and partially defined by the first sensor substrate 200. As shown, the first set 234 of sensors 236 are exposed to the first flow path 240 such that the sample fluid flowing through the first flow path 240 comes into contact with each of the sensors 236 of the first set 234 of sensors 236. As the first set 234 of sensors 236 are shown as aligned along the longitudinal direction 2, the first set 234 of sensors 236 can be substantially aligned with both the first flow path 240 and the first flow direction F1.

The sensor array 10*b* may define a set of passages that transport the sample fluid from the first flow path 240 to the second flow path 246 with these passages located downstream from the first flow path 240. In the depicted embodiment, this includes a first outlet passage 252 that extends from the first flow path 240 substantially along the vertical direction 4 to a first transfer passage 254. The first transfer passage 254, which can extend substantially along the lateral direction 3, extends from the first outlet passage 252 to a second inlet passage 256. The second inlet passage 256 extends substantially along the vertical direction 4 from the first transfer passage 254 to the second flow path 246. Though one particular arrangement of passages is described, it is contemplated that the passages between the first flow path 240 and the second flow path 246 can be differently configured.

The second flow path 246 is located downstream from and in series with the first flow path 240. The second flow path 246 may be substantially open to the second recess 218*b*. The second flow path 246 may extend substantially along the longitudinal direction 2. The second flow path 246 may also extend into the base 204 from the second recess 218*b*. For example, the second flow path 246 may extend from the second inner surface 220*b* towards the second surface 208 and terminate before the second surface 208. The second flow path 246 may define a length along the longitudinal direction 2 that is less than a length of the second recess 218*b* along the longitudinal direction 2. Additionally or alternatively, the second flow path 246 may have a width along the lateral direction 3 that is less than a width of the second recess 218*b* along the lateral direction 3. In this configuration, when the sample fluid flows through the second flow path 246, the sample fluid flows along a second flow direction F2 that is substantially parallel to the longitudinal direction 2 and opposite the first flow direction F1. However, it is contemplated that the second flow path 246 can be differently designed, such that the second flow path 246 and the second flow direction F2 are angularly offset from the longitudinal direction 2, and thus the second flow direction F2 is not opposite the first flow direction F1.

The second flow path may be partially defined by the base 204 and partially defined by the second sensor substrate 202. As a result, the first set 234 of sensors 236 may be exposed to the second flow path 246 such that the sample fluid flowing through the second flow path 246 comes into contact with each of the sensors 236 of the second set 238 of sensors 236. As the second set 238 of sensors 236 are shown as aligned along the longitudinal direction 2, the second set 238 of sensors 236 may be substantially aligned with both the second flow path 246 and the second flow direction F2.

The base 204 may include a second transfer passage 258 that extends from the second flow path 246 to the outlet 260. The outlet 260 may be configured to emit the sample fluid back to the sample analysis system for disposal. As shown, the outlet 260 is defined in the second surface 208 of the base 204 and can be positioned near the first end 210. The outlet 260 is positioned such that the outlet 260 does not overlie either of the first sensor substrate 200 or second sensor substrate 202. Similar to the inlet 248, the outlet 260 may be located elsewhere along the second surface 208, or alternatively along the first surface 206.

In addition, the base 204 can further include a plurality of bores 262 that extend through the base 204 from the first surface 206 to the second surface 208. Each bore 262 may be configured to receive fasteners, such as a screw or a bolt, to releasably or permanently couple the sensor array 10b to the sample analysis system. Though the base 204 is depicted as including twelve bores 262, the base 204 can alternatively include any number or arrangement of bores 262 as desired.

The following exemplary method of using the sensor array 10b is related to a blood draw. It is contemplated that other fluid, liquid and/or gas may be used and blood is not limiting within the disclosure. In operation, the one or more optimization sensor 80 may provide a first usability report of the one or more performance parameters via the one or more physical indicators. The usability report may be, for example, an activated red LED indicating that the sensor array 10b was stored in humid conditions outside of a pre-determined suitable range thus rendering the sensor array 10b unusable and/or inaccurate.

In some embodiments, the one or more optimization sensor 80 may provide a second usability report, in lieu of, or in addition to the first usability report. The second usability report may be provided subsequent to fluid entering of the sensor array 10b. To that end, fluid undergoing analysis enters the inlet 248. The fluid then travels along the first flow path 240 and the second flow path 246 providing access to one or more analyte sensors 236.

Fluid outside of the of flow path (i.e., first flow path 240 and/or second flow path 246) of the sensor array 10b (e.g., due to leak, insufficient bonding) may be detected by the one or more optimization sensor 80. In some embodiments, data provided by the one or more optimization sensor 80 may be provided to the analyzer system 82. The analyzer system 82 may analyze data received from the one or more optimization sensor 80 and determine usability of the sensor array 10b. The analyzer system 82 may provide the second usability report detailing usability of the sensor array 10b. In some embodiments, one or more physical indicators may provide feedback regarding the one or more performance parameters in the second usability report. For example, one or more LED may provide an indication that fluid is outside of the flow path (i.e., first flow path 240 and/or second flow path 246) of the sensor array 10b and the sensor array 10b is rendered inaccurate. The user may discard the sensor array 10b, discard data obtained via the sensor array 10b, or continue analysis of the fluid within the flow path (i.e., first flow path 240 and/or the second flow path 246) of the sensor array 10b.

FIG. 12 is a flow chart 300 of an exemplary method for providing one or more reports of usability and/or quality of one or more sensor array 10. Although the flow chart 300 is directed towards sensor array 10, it is apparent that the steps described may be applied to sensor array 10a and 10b, as well as, variations thereof.

In a step 302, fluid may be obtained and/or provided to the sensor array 10. For example, the fluid may be withdrawn from a patient generally via a syringe or other standard blood draw technique. The fluid may be injected into the fluid inlet 42 and traverse through the flow path 48. In a step 304, the analyzer system 82 may receive data from the one or more optimization sensors 80 of the sensor array 10. In some embodiments. In a step 306, the analyzer system 82 may analyze the data received from the one or more optimization sensors 80 and determine usability and/or quality (e.g., accuracy and/or precision) of the sensor array 10. In a step

308, the analyzer system may provide one or more reports detailing results of the usability and/or quality of the sensor array 10. In some embodiments, one or more physical indicator may provide the one or more reports detailing the results of the one or more performance parameters (e.g., usability and/or quality of the sensor array 10). In a step 310, a decision to discard the sensor array 10 or continue analysis of fluid may be made based on the report and/or results of the usability and/or quality of the sensor array 10.

Many different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub combinations are of utility and may be employed without reference to other features and sub combinations and are contemplated within the scope of the claims. Not all steps listed in the various figures need be carried out in the specific order described.

What is claimed is:

1. A system, comprising:
   a sensor array for analysis of physical parameters and chemical constituents of a volume of fluid, the sensor array comprising:
   a housing
   a fluid inlet;
   a fluid outlet;
   a flow path within the housing and extending between the fluid inlet and fluid outlet;
   at least one sensor positioned within the flow path of the sensor array and configured to provide at least one of a measurement of a physical parameter and a measurement of a chemical constituent of the volume of fluid;
   at least one optimization sensor positioned within the housing and outside of the flow path of the sensor array, the at least one optimization sensor configured to provide at least one measurement correlating to at least one performance parameter of the sensor array; and
   an analyzer system having a processor configured to receive data from the at least one optimization sensor, the analyzer system having a set of instructions stored on at least one non-transitory computer readable medium, the set of instructions directing the processor to:
   analyze measurement data received from the at least one optimization sensor and determine the at least one performance parameter of the sensor array; and,
   provide at least one report of the at least one performance parameter.

2. The system of claim 1, wherein the at least one report directs discarding the sensor array based on the at least one performance parameter.

3. A system, comprising:
   a sensor array for analysis of physical parameters and chemical constituents of a volume of fluid, the sensor array comprising:
   a housing
   a fluid inlet;

a fluid outlet;

a flow path within the housing and extending between the fluid inlet and fluid outlet;

at least one sensor positioned within the flow path of the sensor array and configured to provide at least one of a measurement of a physical parameter and a measurement of a chemical constituent of the volume of fluid;

at least one optimization sensor positioned within the housing and outside of the flow path of the sensor array, the at least one optimization sensor configured to provide at least one measurement correlating to at least one performance parameter of the sensor array; and wherein the at least one performance parameter is a leakage indicator.

4. The system of claim 3, wherein at least one optimization sensor is a proximity sensor and the leakage indicator is detected presence of fluid outside of the flow path.

5. The system of claim 3, wherein at least one optimization sensor is a pressure sensor and the leakage indicator is detected build-up of fluid within the flow path.

6. A system, comprising:

a sensor array for analysis of physical parameters and chemical constituents of a volume of fluid, the sensor array comprising:

a housing a fluid inlet;

a fluid outlet;

a flow path within the housing and extending between the fluid inlet and fluid outlet;

at least one sensor positioned within the flow path of the sensor array and configured to provide at least one of a measurement of a physical parameter and a measurement of a chemical constituent of the volume of fluid;

at least one optimization sensor positioned within the housing and outside of the flow path of the sensor array, the at least one optimization sensor configured to provide at least one measurement correlating to at least one performance parameter of the sensor array; and wherein the at least one performance parameter is an environmental indicator.

7. The system of claim 6, wherein at least one optimization sensor is a thermometer and the environmental indicator is at least one detected temperature measurement outside of a pre-determined threshold.

8. The system of claim 6, wherein at least one optimization sensor is a humidity sensor and the environmental indicator is at least one detected humidity measurement outside of a pre-determined threshold.

9. The system of claim 6, wherein at least one optimization sensor is a corrosion sensor and the environmental indicator is at least one detected corrosion measurement outside of a pre-determined threshold.

10. The system of claim 6, wherein at least one optimization sensor is a light sensor and the environmental indicator is at least one detected wavelength outside of a pre-determined threshold.

11. A sensor array, comprising:

a fluid inlet;

a fluid outlet;

a flow path extending between the fluid inlet and fluid outlet;

at least one optimization sensor positioned outside of the flow path of the sensor array and configured to provide at least one performance parameter of the sensor array, the at least one performance parameter having performance data of the sensor array; and wherein the performance parameter is a leakage indicator.

12. The sensor array of claim 11, wherein the leakage indicator is at least one detected fluid leakage outside of the flow path and detected analyte leakage outside of the flow path.

13. A sensor array, comprising:

a fluid inlet;

a fluid outlet;

a flow path extending between the fluid inlet and fluid outlet;

at least one optimization sensor positioned outside of the flow path of the sensor array and configured to provide at least one performance parameter of the sensor array, the at least one performance parameter having performance data of the sensor array; and wherein the performance parameter is an environmental indicator.

14. The sensor array of claim 13, wherein the environmental indicator is at least one of detected heat, humidity, light and corrosion outside of a pre-determined threshold.

15. A sensor array, comprising:

a fluid inlet;

a fluid outlet;

a flow path extending between the fluid inlet and fluid outlet;

at least one optimization sensor positioned outside of the flow path of the sensor array and configured to provide at least one performance parameter of the sensor array, the at least one performance parameter having performance data of the sensor array; and wherein the at least one optimization sensor positioned outside of the flow path is configured to detect fluid outside of the flow path of the sensor array.

16. The sensor array of claim 15, wherein fluid outside of the flow path of the sensor array is at least one of sample fluid, calibration reagent, wash fluid and quality control fluid.

17. A method, comprising:

providing fluid to an inlet of a sensor array, the sensor array having a housing with an outlet and a flow path extending within the housing from the inlet to the outlet, at least one analyte sensor positioned in the flow path;

receiving data from at least one optimization sensor of the sensor array, the at least one optimization sensor positioned inside the housing and outside of the flow path of the sensor array;

analyzing data from the least one optimization sensor of the sensor array to determine at least one performance parameter of the sensor array;

providing at least one report detailing the at least one performance parameter; and, discarding the sensor array based on the at least one report detailing the at least one performance parameter.

*    *    *    *    *